(12) United States Patent
Strassmann et al.

(10) Patent No.: US 6,368,597 B1
(45) Date of Patent: Apr. 9, 2002

(54) METHODS OF TREATING DIABETES

(75) Inventors: Gideon Strassmann, Washington, DC (US); Li-fang Liang; Stavros Topouzis, both of Elkridge, MD (US)

(73) Assignee: Matamorphix, Inc., Baltimore, MD (US)

( * ) Notice: Subject to any disclaimer, the term of this patent is extended or adjusted under 35 U.S.C. 154(b) by 0 days.

(21) Appl. No.: 09/305,989

(22) Filed: May 6, 1999

(Under 37 CFR 1.47)

Related U.S. Application Data

(60) Provisional application No. 60/084,490, filed on May 6, 1998.

(51) Int. Cl.$^7$ ............................................... A61K 39/395
(52) U.S. Cl. ............................. 424/158.1; 424/130.1; 424/139.1; 424/141.1; 424/145.1; 514/866; 530/300; 530/350; 530/388.1; 530/388.25; 530/388.24; 530/389.1; 530/389.2
(58) Field of Search ............................ 424/130.1, 139.1, 424/141.1, 158.1, 145.1; 435/172.1–172.3, 320.1, 325; 530/300, 350, 388.1, 388.23, 388.24, 389.1, 389.2; 514/866

(56) References Cited

U.S. PATENT DOCUMENTS

| | | | |
|---|---|---|---|
| 5,827,733 A | 10/1998 | Lee et al. | .................... 435/325 |
| 5,994,618 A | * 11/1999 | Lee et al. | ..................... 800/18 |

FOREIGN PATENT DOCUMENTS

| | | |
|---|---|---|
| WO | WO 9421681 | 9/1994 |
| WO | WO 9833887 | 8/1998 |

OTHER PUBLICATIONS

Abel, E. D. et al. "Glucose transporters and pathophysiologic states" *Diabetes Mellitus: A Fundamental and Clinical Text*. LeRoith, D. et al. (eds.) Lippincott–Raven Publishers, Philadelphia: 530–543 (1996).

McPherron, A.C. et al. "Double muscling in cattle due to mutations in the myostatin gene" *Proc Natl Acad Sci U S A* 94(23): 12457–61 (Nov. 11, 1997).

McPherron, A.C. et al. "Regulation of skeletal muscle mass in mice by a new TGF–beta superfamily member" *Nature* 387(6628):83–90 (May 1, 1997).

Das, U.N. "GLUT–4, Tumor Necrosis Factor, Essential Fatty Acids and Daf–genes and Their Role in Insulin Resistance and Non–Insulin Dependent Diabetes Mellitus" *Prostaglandins Leuktrienes and Essential Fatty Acids* 60(1):13–20 (Jan. 1999).

* cited by examiner

*Primary Examiner*—Jeffrey Stucker
*Assistant Examiner*—Ulreke Winkler
(74) *Attorney, Agent, or Firm*—Lahive & Cockfield, LLP; Jane E. Remillard; Maria C. Laccotripe

(57) ABSTRACT

Methods for treating diabetes by administering an inhibitor of GDF-8, or a related member of Transforming Growth Factor-beta (TGF-β) superfamily of structurally-related growth factors (e.g., GDF-11) are disclosed. Also disclosed are methods for upregulating expression of hexose transporters, such as GLUT4 and GLUT1, in a subject by administering an inhibitor of GDF-8. Also disclosed are methods for increasing glucose uptake by cells in a subject, by administering an inhibitor of GDF-8.

7 Claims, 11 Drawing Sheets

METHODS OF TREATING DIABETES

RELATED APPLICATIONS

This application claims priority to U.S. Provisional Application No. 60/084,490, filed May 6, 1998, the entire contents of which are hereby incorporated by reference herein.

BACKGROUND OF THE INVENTION

Diabetes mellitus is the most common metabolic disease worldwide. Every day, 1700 new cases of diabetes are diagnosed in the United States, and at least one-third of the 16 million Americans with diabetes are unaware of it. Diabetes is the leading cause of blindness, renal failure, and lower limb amputations in adults and is a major risk factor for cardiovascular disease and stroke.

Normal glucose homeostasis requires the finely tuned orchestration of insulin secretion by pancreatic beta cells in response to subtle changes in blood glucose levels, delicately balanced with secretion of counter-regulatory hormones such as glucagon. Type 1 diabetes results from autoimmune destruction of pancreatic beta cells causing insulin deficiency. Type 2 or noninsulin-dependent diabetes mellitus (NIDDM) accounts for >90% of cases and is characterized by a triad of (1) resistance to insulin action on glucose uptake in peripheral tissues, especially skeletal muscle and adipocytes, (2) impaired insulin action to inhibit hepatic glucose production, and (3) dysregulated insulin secretion (DeFronzo, (1997) Diabetes Rev. 5:177–269). In most cases, type 2 diabetes is a polygenic disease with complex inheritance patterns (reviewed in Kahn et al., (1996) Annu. Rev. Med. 47:509–531).

Environmental factors, especially diet, physical activity, and age, interact with genetic predisposition to affect disease prevalence. Susceptibility to both insulin resistance and insulin secretory defects appears to be genetically determined (Kahn, et al). Defects in insulin action precede the overt disease and are seen in nondiabetic relatives of diabetic subjects. In spite of intense investigation, the genes responsible for the common forms of Type 2 diabetes remain unknown.

One of the fundamental actions of insulin is to stimulate uptake of glucose from the blood into tissues, especially muscle and fat. This occurs via facilitated diffusion which is mediated by specific glucose transporter proteins that insert into the plasma membrane of cells. GLUT4 is the most important insulin-sensitive glucose transporter in these tissues. Insulin binds to its receptor in the plasma membrane, generating a series of signals that result in the translocation or movement of GLUT4 transporter vesicles to the plasma membrane, where a first docking step, followed by fusion with the plasma membrane takes place; after an activation or exposure step takes place, glucose enters the cell. Studies in both animals and humans indicate that alterations in GLUT4 expression, trafficking, and/or activity occur in adipose cells and muscle in diabetes and other insulin-resistant states (Abel et al., Diabetes Mellitus: A Fundamental and Clinical Text (1996) pp.530–543.)

New and innovative treatments for diabetes are clearly a priority for researchers in this field. The present invention provides such innovative treatments, taking advantage of the knowledge concerning GLUT4 expression and activity, and expression and activity of related hexose transporters (e.g., GLUT1).

SUMMARY OF THE INVENTION

The present invention provides a method of treating diabetes and related diseases, such as obesity, by administering to a subject an inhibitor of GDF-8. Suitable inhibitors of GDF-8 which can be employed in the methods of the invention include, but are not limited to, GDF-8 peptides (e.g., derived from the pro-domain), GDF-8 dominant-negative mutants, antibodies and antibody fragments which bind to GDF-8 (or the receptor for GDF-8) and inhibit GDF-8 binding to its receptor, GDF-8 receptor peptide antagonists, antisense nucleic acids directed against GDF-8 mRNA and anti-GDF-8 ribozymes.

In another aspect, the present invention provides a method of increasing GLUT4 expression in a cell (e.g., a muscle cell or a fat cell in a subject), or increasing glucose uptake by a cell, by administering a GDF-8 inhibitor. Such methods can be used, not only to treat diabetes and related diseases, but also to treat several systemic problems resulting from insufficient glucose metabolism, such as hyperglycemia.

The methods of the present invention also can be performed using as targets other TGF-β growth factors which are related in structure and activity to GDF-8, such as GDF-11. Accordingly, in another embodiment, the invention provides method of treating diabetes by administering to a subject an inhibitor of GDF-11, either alone or in combination with other GDF inhibitors (e.g., an inhibitor of GDF-8).

DETAILED DESCRIPTION OF THE INVENTION

Figure 1A:
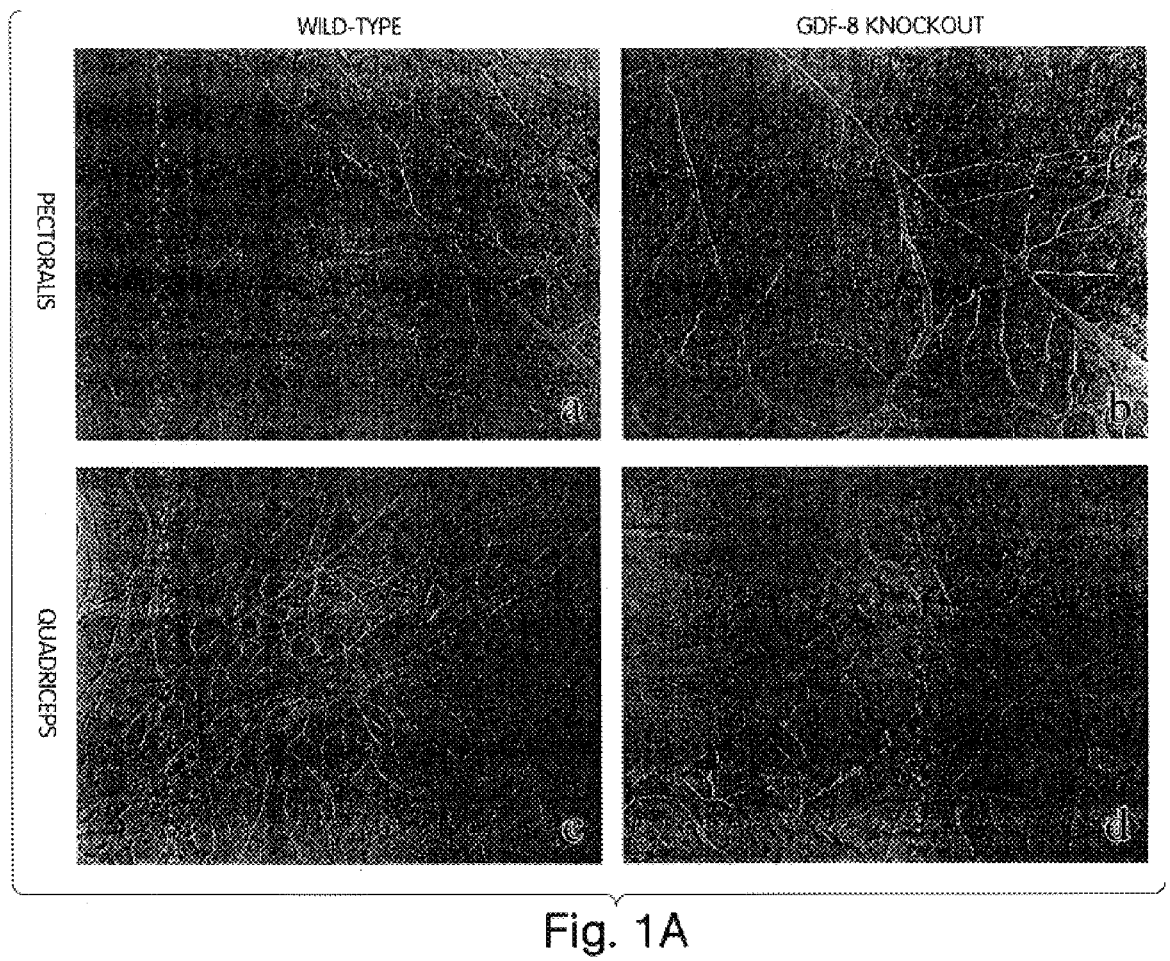
FIG. 1A shows GLUT4 levels by immunostaining, with an anti-GLUT4 antibody, in the pectoralis and the quadriceps from a wild-type mouse and a GDF-8 knockout mouse.

The present invention is based, in part, on the discovery that GDF-8 downregulates expression of GLUT4 in tissues primarily in muscle and fat. Regulation of glucose metabolism by insulin is a key mechanism by which homeostasis is maintained in an animal. The action of insulin in the regulation of circulating glucose levels is to stimulate glucose uptake in muscle and fat tissues. Insulin stimulates glucose uptake in these tissues by increasing the translocation of GLUT4, the insulin-sensitive glucose transporter, from an intracellular vesicular compartment to the plasma membrane.

It was further discovered as part of the present invention that GLUT4 expression in muscle and fat cells can be upregulated by inhibiting GDF-8. It was also discovered that glucose uptake by these cells can be increased by inhibiting GDF-8. These effects can be advantageously utilized to treat a variety of metabolic diseases resulting from dysfunctional glucose metabolism (e.g., hyperglycemia) and/or insulin resistance.

Accordingly, in one embodiment, the present invention provides a method for treating diabetes mellitus and related disorders, such as obesity or hyperglycemia, by administering to a subject an inhibitor of GDF-8 in an amount sufficient to ameliorate the symptoms of the disease. Type 2 or noninsulin-dependent diabetes mellitus (NIDDM), in particular, is characterized by a triad of (1) resistance to insulin action on glucose uptake in peripheral tissues, especially skeletal muscle and adipocytes, (2) impaired insulin action to inhibit hepatic glucose production, and (3) dysregulated insulin secretion (DeFronzo, (1997) Diabetes Rev. 5:177-269). Therefore, subjects suffering from type 2 diabetes can be treated according to the present invention by administration of a GDF-8 inhibitor, which increases sensitivity to insulin and glucose uptake by cells.

Similarly, other diseases characterized by insulin dysfunction (e.g., resistance, inactivity or deficiency) and/or insufficient glucose transport into cells also can be treated according to the present invention by administration of a GDF-8 inhibitor, which increases sensitivity to insulin and glucose uptake by cells.

Definitions

As used herein, the term "GDF-8 inhibitor" or "an inhibitor of GDF-8" includes any agent capable of inhibiting GDF-8 activity, including but not limited to peptides (derived from GDF-8, GDF-11 or other unrelated sequences), dominant-negative protein mutants, peptidomimetics, antibodies or fragments thereof, ribozymes, antisense oligonucleotides, or other small molecules which specifically inhibit the action of GDF-8 while, preferably, leaving intact the activity of TGF-β, Activin or other members of the TGF-β superfamily. The term "a GDF-11 inhibitor" also encompasses these classes of inhibitors and, preferably, specifically inhibits GDF-11. GDF-8 and GDF-11 are structurally and functionally related members of the TGF-β family of growth factors.

GDF-8 inhibitors used in the methods of the invention, particularly those derived from GDF-8 itself (e.g., GDF-8 peptides, such as the pro-domain or portions thereof), preferably do not possess GDF-8 activity. Such inhibitors and methods for their identification are described in U.S. Ser. No. 60/116,639, entitled "Growth Differentiation Factor Inhibitors and Uses Therefor", incorporated by reference herein in its entirety. For example, the inhibitory action of a GDF-8 inhibitor can be assessed using a variety of art-recognized assays, such as a Northern blot analysis of GDF-8 mRNA, or a Western blot analysis or immunostaining analysis of GDF-8 protein levels, among others. Identified GDF-8 inhibitory compounds can be further evaluated, detected, cloned, sequenced, and the like, either in solution or after binding to a solid support, by any method usually applied to the detection of a specific DNA sequence such as PCR, oligomer restriction (Saiki et al., Bio/Technology, 3:1008 (1985)), allele-specific oligonucleotide (ASO) probe analysis (Conner et al., Proc. Natl. Acad. Sci. USA 80:278 (1983)), ligase-mediated gene detection (Landegren et al, Science 241:1077 (1988)), and the like.

As used herein, the term "GDF-8 activity" or "GDF-11 activity" includes any activity mediated by GDF-8 or GDF-11, respectively. For example, GDF-8 is known to inhibit fibroblast differentiation to adipocytes, modulate the production of muscle-specific enzymes, e.g., creatine kinase, modulate uptake glucose by cells, and stimulate myoblast cell proliferation. Accordingly, the degree to which a GDF-8 inhibitor prevents GDF-8 activity can be identified by, for example, testing for the ability of the inhibitor to block GDF-8 activity, as measured by the ability of GDF-8 to interfere with the differentiation process of 3T3-L1 pre-adipocytes (fibroblasts) to adipocytes, the ability to modulate the activity of muscle-specific enzymes, e.g., creatine kinase, the ability to modulate glucose uptake by cells, or the ability to stimulate myoblast cell proliferation. The effect of the inhibitor on inhibition of insulin stimulation of GLUT4 expression and glucose uptake, can also be assessed, and may include measurements before and after incubating in the presence of the compound.

As used herein, the term "modulate" refers to an increase in function. For example, modulation of gene transcription or expression refers to upregulation of these functions. Modulation of protein activity refers to an increase in activity.

As used herein, the term "inhibit" refers to a decrease, whether partial or whole, in function. For example, inhibition of gene transcription or expression refers to any level of downregulation of these functions, including complete elimination of these functions. Modulation of protein activity refers to any decrease in activity, including complete elimination of activity.

As used herein, the term "diabetes" includes all known forms of diabetes, including type I and type II diabetes, as described in Abel et al., Diabetes Mellitus: A Fundamental and Clinical Text (1996) pp.530–543.

GDF-8 inhibitors of the invention are typically administered to a subject in "substantially pure" form. The term "substantially pure" as used herein refers to GDF-8 which is substantially free of other proteins, lipids, carbohydrates, or other materials with which it is naturally associated. One skilled in the art can purify GDF-8 using standard techniques for protein purification. The substantially pure polypeptide will yield a single major band on a non-reducing polyacrylamide gel. The purity of the GDF-8 polypeptide can also be determined by amino-terminal amino acid sequence analysis.

Specific details on the production of GDF-8 for testing and developing inhibitors for use in the present invention are provided by McPherron, et al., Nature 387:83 90 (1997), and U.S. Pat. No. 5,827,733, both hereby incorporated by reference in their entirety.

As used herein, the term "hexose transporter" includes integral membrane proteins of a cell able to transport a hexose sugar, such as glucose, from the exterior to the interior of the cell. Examples of such transporters are the GLUT1 and GLUT4 transporter proteins, among others, in muscle and fat cells.

As used herein, the term "modulation of GDF-8 activity" or "modulation of GDF-8 level" refers to a change in GDF-8 activity or level compared to its native state. This change may be either positive (upregulation), or negative (downregulation), but for the purposes of the present invention is preferably the latter.

Cells which are targeted by the methods of the present invention, such as muscle and fat cells, include isolated cells maintained in culture as well as cells within their natural context in vivo (e.g., in fat tissue or muscle tissue, such as pectoralis, triceps, gastrocnemius, quadriceps, and iliocostal muscles).

The term "antisense nucleic acid" refers to a DNA or RNA molecule that is complementary to at least a portion of a specific mRNA molecule (Weintraub, Scientific American 262:40 (1990)). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target GDF-8 producing cell. The use of antisense methods to inhibit the in vitro translation of genes is well known in the art (Marcus-Sakura, Anal. Biochem.172:289 (1988)).

As used herein, a "ribozyme" is a nucleic acid molecule having nuclease activity for a specific nucleic acid sequence. A ribozyme specific for GDF-8 mRNA, for example, would bind to and cleave specific regions of the GDF-8 mRNA, thereby rendering it untranslatable and resulting in lack of GDF-8 polypeptide production.

The term "dominant-negative mutant" refers to a GDF-8 protein which has been mutated from its natural state and which interacts with GDF-8 or a GDF-8 gene, thereby inhibiting its production and/or activity.

The "antibodies" of the present invention include antibodies immunoreactive with GDF-8 polypeptides or functional fragments thereof. Antibodies which consist essentially of pooled monoclonal antibodies with different epitopic specificities, as well as distinct monoclonal antibody preparations are provided. Monoclonal antibodies are made from antigen-containing fragments of the protein by methods well known to those skilled in the art (Kohler et al, Nature 256:495(1975)). The term "antibody" as used in this invention is meant to include intact molecules as well as fragments thereof, such as Fab and F(ab')$_2$, Fv and SCA fragments which are capable of binding an epitopic determinant on GDF-8.

A "Fab fragment" consists of a monovalent antigen-binding fragment of an antibody molecule, and can be produced by digestion of a whole antibody molecule with the enzyme papain, to yield a fragment consisting of an intact light chain and a portion of a heavy chain.

A "Fab' fragment" of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

A "(Fab')$_2$" of an antibody can be obtained by treating a whole antibody molecule with the enzyme pepsin, without subsequent reduction. A (Fab')$_2$ fragment is a dimer of two Fab' fragments held together by two disulfide bonds.

An "Fv fragment" is defined as a genetically engineered fragment containing the variable region of a light chain and the variable region of a heavy chain expressed as two chains.

A "single chain antibody" (SCA) is a genetically engineered single chain molecule containing the variable region of a light chain and the variable region of a heavy chain, linked by a suitable, flexible polypeptide linker.

GDF-8 and GDF-11 Inhibitors for Use in the Methods of the Invention

GDF-8 inhibitors suitable for use in the invention include, but are not limited to, peptides, including peptides derived from GDF-8 (e.g., mature GDF-8 or the pro-domain of GDF-8) or non-GDF-8 peptides, GDF-8 dominant-negative mutants, antibodies and antibody fragments which bind to GDF-8 (or the receptor for GDF-8) and inhibit GDF-8 binding to its receptor, GDF-8 receptor peptide antagonists, antisense nucleic acids directed against GDF-8 mRNA and anti-GDF-8 ribozymes. Thus, GDF-8 inhibitors can act at the message (transcription) level or at the protein (expression or activity) level.

As used herein, the term "GDF-8" includes all known forms of GDF-8 including but not limited to human GDF-8, bovine GDF-8, chicken GDF-8, murine GDF-8, rat GDF-8, porcine GDF-8, ovine GDF-8, turkey GDF-8, and baboon GDF-8. These molecules are described in McPherron A. C. et al. (1997) *Proc. Natl. Acad Sci.* 94:12457–12461, the contents of which are incorporated herein by reference. The amino acid sequences for these proteins are shown in FIG. 12.

As used herein, the term "GDF-11" includes all known forms of GDF-11 including but not limited to human GDF-11, bovine GDF-11, chicken GDF-11, murine GDF-11, rat GDF-11, porcine GDF-11, ovine GDF-11, turkey GDF-11, and baboon GDF-11.

GDF-8 and GDF-11 inhibitory peptides can be identified and isolated from media of cells expressing GDF-8 or GDF-11 using techniques known in the art for purifying peptides or proteins including ion-exchange chromatography, gel filtration chromatography, ultrafiltration, electrophoresis, and immunoaffinity purification with antibodies specific for the GDF-8 or GDF-11 inhibitor, or a portion thereof. In one embodiment, the media obtained from cultures of cells which express GDF-8 or GDF-11 are subjected to high performance liquid chromatography (HPLC). The samples obtained can then be tested for GDF-8 or GDF-11 inhibitory activity as described below.

Alternatively, GDF-8 and GDF-11 peptide inhibitors can be identified by screening fragments of GDF-8 or GDF-11 for inhibitory activity. GDF-8 or GDF-11 fragments can be produced by a variety of art known techniques. For example, specific oligopeptides (approximately 10–25 amino acids-long) spanning the GDF-8 or GDF-11 sequence can be synthesized (e.g., chemically or recombinantly) and tested for their ability to inhibit GDF-8 or GDF-11, for example, using the assays described herein. The GDF-8 or GDF-11 peptide fragments can be synthesized using standard techniques such as those described in Bodansky, M. *Principles of Peptide Synthesis,* Springer Verlag, Berlin (1993) and Grant, G. A (ed.). *Synthetic Peptides: A User's Guide,* W. H. Freeman and Company, New York (1992). Automated peptide synthesizers are commercially available (e.g., Advanced ChemTech Model 396; Milligen/Biosearch 9600).

Alternatively, GDF-8 or GDF-11 fragments can be produced by digestion of native or recombinantly produced GDF-8 or GDF-11 by, for example, using a protease, e.g., trypsin, thermolysin, chymotrypsin, or pepsin. Computer analysis (using commercially available software, e.g. MacVector, Omega, PCGene, Molecular Simulation, Inc.) can be used to identify proteolytic cleavage sites.

GDF-8 or GDF-11 inhibitors used in the methods of the invention are preferably isolated. As used herein, an "isolated" or "purified" protein or biologically active peptide thereof is substantially free of cellular material or other contaminating proteins from the cell or tissue source from which the GDF-8 or GDF-11 protein or peptide is derived, or substantially free from chemical precursors or other chemicals when chemically synthesized. The language "substantially free of cellular material" includes preparations of GDF-8 or GDF-11 protein or peptide thereof in which the protein or peptide thereof is separated from cellular components of the cells from which it is isolated or recombinantly produced. In one embodiment, the language "substantially free of cellular material" includes preparations of GDF-8 or GDF-11 protein or peptide thereof having less than about 30% (by dry weight) of non-GDF-8 or GDF-11 protein or peptide thereof (also referred to herein as a "contaminating protein"), more preferably less than about 20% of non-GDF-8 or GDF-11 protein or peptide thereof, still more preferably less than about 10% of non-GDF-8 or GDF-11 protein or peptide thereof, and most preferably less than about 5% non-GDF-8 or GDF-11 protein or peptide thereof. When the GDF-8 or GDF-11 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

A two-step method can be used to produce and isolate such proteolytically cleaved GDF-8 or GDF-11 peptides. The first step involves enzymatic digestion of the GDF-8 or GDF-11 protein. GDF-8 or GDF-11 can be produced either as a dimer from CHO cell conditioned media, as a monomer in *E. coli* or yeast, or isolated from cells which naturally produce GDF-8 or GDF-11. Following purification of GDF-8 or GDF-11 monomers or dimers by, for example, HPLC chromatography, their enzymatic digestion is performed as described infra. The amino acids cleaved during the digestion depend on the specific protease used in the experiment as is known in the art. For example, if the protease of choice were trypsin, the cleavage sites would be amino acids arginine and lysine. The GDF-8 or GDF-11 protein can be digested using one or more of such proteases.

After the digestion, the second step involves the isolation of peptide fractions generated by the protein digestion. This can be accomplished by, for example, high resolution peptide separation as described infra. Once the fractions have been isolated, their GDF-8 or GDF-11 inhibitory activity can be tested for by an appropriate bioassay, as described below.

The proteolytic or synthetic GDF-8 or GDF-11 fragments can comprise as many amino acid residues as are necessary to inhibit, e.g., partially or completely, GDF-8 or GDF-11 function, and preferably comprise at least 5, 10, 15, 20, 25, 30, 35, 40, 45, 50, 55, 60, 65, 70, 75, 80, 85, 90, 95, 100 or more amino acids in length.

In one embodiment, peptides are selected which do not contain a sufficient number of T cell epitopes to induce T cell mediated immune responses and/or which contain a sufficient number of B cell epitopes to elicit antibodies when administered to a mammal. Preferred GDF-8 or GDF-11 peptide inhibitors do not contain a sufficient number of T cell epitopes to induce T-cell mediated (e.g., cytokine) responses. However, B cell epitopes may be desirable and can be selected for by, for example, testing the peptide's ability to elicit an antibody response, as discussed below.

T cell epitopes within GDF-8 or GDF-11 fragments can be identified using a number of well known techniques. For example, T cell epitopes can be predicted using algorithms (see e.g., Rothbard, J. and Taylor, W. R. (1988) *EMBO J.* 7:93–100; Berzofsky, J. A. (1989) *Philos Trans R. Soc. Lond.* 323:535–544). Preferably, human T cell epitopes within a GDF-8 or GDF-11 protein can be predicted using known HLA class II binding specific amino acid residues. One algorithm for predicting peptides having T cell stimulating activity which has been used with success is reported in Rothbard, 1st *Forum in Virology, Annals of the Pasteur Institute,* pp 518–526 (December, 1986), Rothbard and Taylor, (1988) *Embo,* 7:93–100 and EP 0 304 279. These documents report defining a general T cell pattern (algorithm), its statistical significance and its correlation with known epitopes as well as its successful use in predicting previously unidentified T cell epitopes of various protein antigens and autoantigens. The general pattern for a T cell epitope as reported in the above-mentioned documents appears to contain a linear patter composed of a charged amino acid residue or glycine followed by two hydrophobic residues. Other algorithms that have been used to predict T cell epitopes of previously undefined proteins include an algorithm reported by Margalit et al., (1987) *J. Immunol.,* 138:2213–2229, which is based on an amphipathic helix model.

Other methods for identifying T cell epitopes involve screening GDF-8 or GDF-11 inhibitory peptides of the invention for human T cell stimulating activity. This can be accomplished using one or more of several different assays. For example, in vitro, T cell stimulatory activity can be assayed by contacting a peptide of the invention with an antigen presenting cell which presents appropriate MHC molecules in a T cell culture. Presentation of a GDF-8 or GDF-11 inhibitory peptide of the invention in association with appropriate MHC molecules to T cells, in conjunction with the necessary costimulation can have the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA,* 86:1333 (1989) the entire contents of which are incorporated herein by reference. A kit for an assay for the production of interferon is also available from Genzyme Corporation (Cambridge, Mass.).

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Other preferred peptide inhibitors of GDF-8 or GDF-11 are located on the surface of the GDF-8 and GDF-11 proteins, e.g., hydrophilic regions, as well as regions with high antigenicity or fragments with high surface probability scores can be identified using computer analysis programs well known to those of skill in the art (Hopp and Wood, (1983), Mol. Immunol., 20,483–9, Kyte and Doolittle, (1982), J. Mol. Biol., 157, 105–32, Corrigan and Huang, (1982), Comput. Programs Biomed, 3, 163–8).

Still other preferred peptides of GDF-8 or GDF-11 to be tested for GDF-8 or GDF-11 inhibitory activity include one or more B-cell epitopes. Such peptides can be identified by immunizing a mammal with the peptide, either alone or combined with or linked to an adjuvant (e.g., a hapten), and testing sera from the immunized animal for anti-GDF-8 or GDF-11 antibodies. Preferred peptides generate anti-GDF-8 or GDF-11 antibodies which inhibit GDF-8 or GDF-11 activity, indicating that these peptides are somehow related to the protein's activity (e.g., correspond to all or a portion of the active site). For example, sera from immunized animals can be tested for GDF-8 or GDF-11 inhibitory activity using any of the GDF-8 or GDF-11 bioassays described herein.

Alternatively, anti-GDF-8 or anti-GDF-11 antibodies or antibody fragments can be administered directly to a subject to inhibit GDF-8 or GDF-11 activity. Preferred antibodies include monoclonal antibodies, including humanized, chimeric and human monoclonals or fragments thereof.

To generate such antibodies, a proteolytic or synthetic GDF-8 or GDF-11 fragment (alone or linked to a suitable carrier or hapten) can be used to immunize a subject (e.g., a mammal including, but not limited to a rabbit, goat, mouse or other mammal). For example, the methods described in U.S. Pat. Nos. 5,422,110; 5,837,268; 5,708,155; 5,723,129; and 5,849,531, can be used and are incorporated herein by reference. In a preferred embodiment, the mammal being immunized does not contain endogenous GDF-8 or GDF-11 (e.g., a GDF-8 or GDF-11 knock-out transgenic animal). The immunogenic preparation can further include an adjuvant, such as Freund's complete or incomplete adjuvant, or similar immunostimulatory agent. Immunization of a suitable subject with an immunogenic proteolytic or synthetic GDF-8 or GDF-11 fragment preparation induces a polyclonal anti-GDF-8 or GDF-11 antibody response. The anti-GDF-8 or GDF-11 antibody titer in the immunized subject can be monitored over time by standard techniques, such as with an enzyme linked immunosorbent assay (ELISA) using immobilized GDF-8 or GDF-11. Subsequently, the sera from the immunized subjects can be tested for their GDF-8 or GDF-11 inhibitory activity using any of the bioassays described herein.

Alternatively, is also possible to immunize subjects (e.g., GDF-8 and GDF-11 knockout mice) with plasmids expressing GDF-8 and GDF-11 using DNA immunization technology, such as that disclosed in U.S. Pat. No. 5,795,872, Ricigliano et al., "DNA construct for immunization" (1998), and in U.S. Pat. No. 5,643,578, Robinson et al., "Immunization by inoculation of DNA transcription unit" (1997).

The antibody molecules directed against GDF-8 or GDF-11 can be isolated from the mammal (e.g., from the blood) and further purified by well known techniques, such as protein A chromatography to obtain the IgG fraction. At an appropriate time after immunization, e.g., when the anti-GDF-8 or GDF-11 antibody titers are highest, antibody-producing cells can be obtained from the subject and used to prepare e.g., monoclonal antibodies by standard techniques, such as the hybridoma technique originally described by Kohler and Milstein (1975) *Nature* 256:495–497) (see also, Brown et al. (1981) *J. Immunol* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a GDF-8 or GDF-11 immunogen as described above, and the culture supernatants of the resulting hybridoma cells are screened to identify a hybridoma producing a monoclonal antibody that binds GDF-8 or GDF-11.

Any of the many well known protocols used for fusing lymphocytes and immortalized cell lines can be applied for the purpose of generating an anti-GDF-8 or GDF-11 monoclonal antibody (see, e.g., G. Galfre et al. (1977) *Nature* 266:55052; Gefter et al. *Somatic Cell Genet.*, cited supra; Lerner, Yale *J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind GDF-8 or GDF-11, e.g., using a standard ELISA assay. The antibodies can then be tested for GDF-8 or GDF-11 inhibitory activity using, for example, the assays described herein.

In another aspect of the invention, GDF-8 protein fragments comprise all or a portion of the GDF-8 pro-domain. The pro-domain of TGF-β has been shown to have inhibitory activity against the mature active TGF-β (Bottinger et. al., (1996) *PNAS*, 93, 5877–5882; Gentry and Nash, (1990) *Biochemistry*, 29, 6851–6857). Since GDF-8 is a member of the TGF-β superfamily, the pro-domain of GDF-8 may also act as an inhibitor to the active GDF-8. The pro-domain of GDF-8 can be generated by expressing it using various expression systems (e.g. CHO, baculovirus and the like). The expressed pro-domain of GDF-8 can be purified by, for example, using the method described in Bottinger et. al. (supra) or any other art recognized method for purifying peptides. Alternatively, the pro-domain can be tagged to, for example, FLAG or 6-His, as described below.

Based on the information obtained for TGF-β, peptide fragments that span the C-terminus of the mature GDF-8 can be designed and synthesized. Preferably, the GDF-8 peptide fragments are about 25 amino acids long. In other preferred embodiments, the GDF-8 peptide fragments can have a sequence length of about, 20–25, 25–30, 30–35, 35–40, or 40–45 amino acid residues in length. The GDF-8 peptide fragments modeled after the aforementioned pentacosapeptide can then be tested for GDF-8 or GDF-11 inhibitory activity using the assays described herein.

GDF-8 or GDF-11 inhibitors for use in the methods of the present invention can be identified using a variety of appropriate bioassays which test for the inhibition of GDF-8 or GDF-11 activity. The ability of the GDF-8 or GDF-11 inhibitors to inhibit GDF-8 or GDF-11 activity is preferably specific, i.e., the GDF-8 inhibitor can specifically inhibit the GDF-8 protein and the GDF-11 inhibitor can specifically inhibit the GDF-11 protein. In certain embodiments, the GDF-8 inhibitor is also able to inhibit GDF-11 activity and the GDF-11 inhibitor is also able to inhibit GDF-8 activity.

As used herein, the term "bioassay" includes any assay designed to identify a GDF-8 or GDF-11 inhibitor. The assay can be an in vitro or an in vivo assay suitable for identifying whether a GDF-8 or GDF-11 inhibitor can inhibit one or more of the biological fuictions of GDF-8 or GDF-11. Examples of suitable bioassays include DNA replication assays, transcription-based assays, creatine kinase assays, assays based on the differentiation of 3T3-L1 pre-adipocytes, assays based on glucose uptake control in 3T3-L1 adipocytes, and immunological assays (described in subsection II).

It has been established that GDF-8 modulates the protein levels, and therefore the activity, of a muscle-specific enzyme, creatine kinase. This effect of GDF-8 or GDF-11 can be used to screen fractions that contain potential GDF-8 or GDF-11 inhibitors. This assay can be performed in the mouse skeletal myoblast cell line C1C12 or in primary chick myoblast isolated from Day 11 chick embryos. Cells are grown in 48-well trays in serum-containing medium that maintains them undifferentiated. When a 70% confluence has been reached, medium is switched to 1% serum, thus allowing differentiation and creatine kinase expression. At the time of the switch, the potential GDF-8 or GDF-11-inhibitory fraction is added to some wells, followed some time later by GDF-8 or GDF-11 itself. Cells are returned to the incubator for an additional two to three day period. In the end, cells are lysed and creatine kinase activity is measured in the lysates using a commercially available kit (available by Sigma, St Louis, Mo.).

Uses

In one embodiment, the method of the invention can be used either in vitro or in vivo to modulate (i.e., upregulate) the expression of a hexose transporter, such as GLUT4 or GLUT1, in a cell which expresses these transporters, such as a muscle and/or fat cell. This is achieved by inhibiting the activity or expression of GDF-8 or GDF-11 in the cell or outside the cell.

In another embodiment, the method of the invention can be used either in vitro or in vivo to increase insulin sensitivity and/or glucose uptake by a cell.

In another embodiment, the method of the invention can be used to treat a disease characterized by insufficient GLUT4 expression, insulin dysfunction (e.g., resistance, inactivity or deficiency) and/or insufficient glucose transport into cells. Such diseases include, but are not limited to diabetes, hyperglycemia and obesity.

In another embodiment, the method of the invention can be used to create a novel in vitro model, in which GDF-8 is utilized to examine glucose uptake or glucose metabolism in adipocytes. GDF-8, which is specifically expressed in muscle and fat in vivo, inhibits 3T3-L1 adipocyte differentiation by directly or indirectly suppressing the expression of adipocyte-specific genes, e.g. the GLUT4 transporter. GDF-8 can, therefore, be used as a prototype regulator of these genes in the 3T3-L1 cell system. This system can be a model for understanding the role of GDF-8 on the regulation of adipocyte-specific gene expression and protein activity of molecules such as, but not limited to, transcription factors, signal transduction proteins, leptin, fatty acid binding protein, fatty acid synthase, peroxisome proliferator-activated receptors, uncoupling proteins 1 and 2, and molecules that are activated, inactivated, or modified by the actions of GDF-8.

Other uses for the methods of the invention will be apparent to one of ordinary skill in the art from the following Examples and Claims.

Administration of GDF-8 and GDF-11 Inhibitors in Pharmaceutical Compositions

GDF-8 and GDF-11 inhibitors used in the methods of the present invention are generally administered to a subject in the form of a suitable pharmaceutical composition. Such compositions typically contain the inhibitor and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the GDF-8 inhibitor, use thereof in the compositions is contemplated. Supplementary active compounds can also be incorporated into the compositions.

A pharmaceutical composition of the invention is formulated to be compatible with its intended route of administration. Examples of suitable routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the GDF-8 inhibitor in the required amount in an appropriate solvent with one or a combination of ingredients enumerated above, as required, followed by filtered sterilization. Generally, dispersions are prepared by incorporating the GDF-8 inhibitor into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the GDF-8 inhibitor can be incorporated with excipients and used in the form of tablets, troches, or capsules, oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The GDF-8 inhibitor can also be prepared in the form of suppositories (e.g., with conventional suppository bases such as cocoa butter and other glycerides) or retention enemas for rectal delivery.

In one embodiment, the GDF-8 inhibitors are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. GDF-8 inhibitors which exhibit large therapeutic indices are preferred. While GDF-8 inhibitors that exhibit toxic side effects may be used, care should be taken to design a delivery system that targets such GDF-8 inhibitors to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any GDF-8 inhibitor used in the method of the invention, the therapeutically effective dose can be estimated initially from cell culture assays. A dose may be formulated in animal models to achieve a circulating plasma concentration range that includes the $IC_{50}$ (i.e., the concentration of the test GDF-8 inhibitor which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

The GDF-8 inhibitors of the present invention, e.g., the anti-sense oligonucleotide inhibitors, can further be inserted into vectors and used in gene therapy. Gene therapy vectors can be delivered to a subject by, for example, intravenous injection, local administration (see U.S. Pat. No 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Vectors suitable for use in gene therapy are known in the art. For example, adenovirus-derived vectors can be used. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology,* E. J. Murray, Ed. (Humana, Clifton, N.J., 1991) vol. 7. pp. 109–127). Expression of the gene of interest comprised in the nucleic acid molecule can be under control of, for example, the E1A promoter, the major late promoter (MLP) and associated leader sequences, the E3 promoter, or exogenously added promoter sequences.

Yet another viral vector system useful for delivery of the GDF-8 inhibitors of the invention is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). Adeno-associated viruses exhibit a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as few as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into T cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790). Other viral vector systems that may be useful for delivery of the GDF-8 inhibitors of the invention are derived from herpes virus, vaccinia virus, and several RNA viruses.

The following examples are intended to illustrate but not limit the invention. While they are typical of those that might be used, other procedures known to those skilled in the art may alternatively be used.

Exemplification

Materials and Methods

The following studies were performed at Intracel (Rockville, Md.) using six week old male Balb/c mice. GDF-8 knockout and wild-type (control) mice were obtained from Dr. S. J. Lee (Johns Hopkins University, See McPherron et al., *Nature* 387:83–90 (1997)).

Recombinant human GDF-8 was produced in Chinese Hamster Ovarian (CHO) cells. The secreted protein was purified using several steps of chromatography to obtain substantially homogeneous GDF-8.

Other materials and methods are described in the Examples below.

EXAMPLE 1

Effect of GDF-8 Knockout on GLUT4 Protein Expression in Muscle Cells

To assess the impact on protein expression of the muscle cell glucose transporter, GLUT4, of knocking out natural GDF-8 expression, samples of various muscles were taken from both wild-type and GDF-8 knockout mice. Muscle samples were fixed in 10% (v/v) neutral buffered formaldehyde (StatLab, Lewisville, Tex.) for 8 hours at room temperature followed by embedding in Paraplast® X-tra tissue-embedding medium (Oxford Labware, St. Louis, Mo.). Cross sections of mouse muscle samples were prepared. Slides were preheated in an oven at 60° C. for at least 30 min prior to GLUT4 immunodetection. Paraffin sections were deparaffinzed in xylene three times, 5 min each. Sections were rehydrated and then blocked with 20% normal goat serum (Vector, Burlingame, Calif.) in "Antibody Diluent" (DAKO, Carpinteria, Calif.) for 20 minutes. Sections were incubated with rabbit anti-GLUT4 (Alpha Diagnostic International, San Antonio, Tex.) diluted in Antibody Diluent at a concentration of 2 µg/ml overnight at room temperature. Sections were rinsed with OptiMax Wash Buffer (Biogenex, San Ramon, Calif.) and incubated with biotinylated goat anti-rabbit immunoglobulin (BioGenex) for conjugated streptavidin (BioGenex) for 30 min. Sections were rinsed with the wash buffer and then DAB substrate (DAKO) was applied for visualizing the antibody binding sites. Sections were counterstained with methyl green (DAKO) and mounted using Cytoseal™ 60 (Stephens Scientific, Riverdale, N.J.). Brown staining indicates the expression of GLUT4 and green staining identifies the nucleus.

Figure 1B:
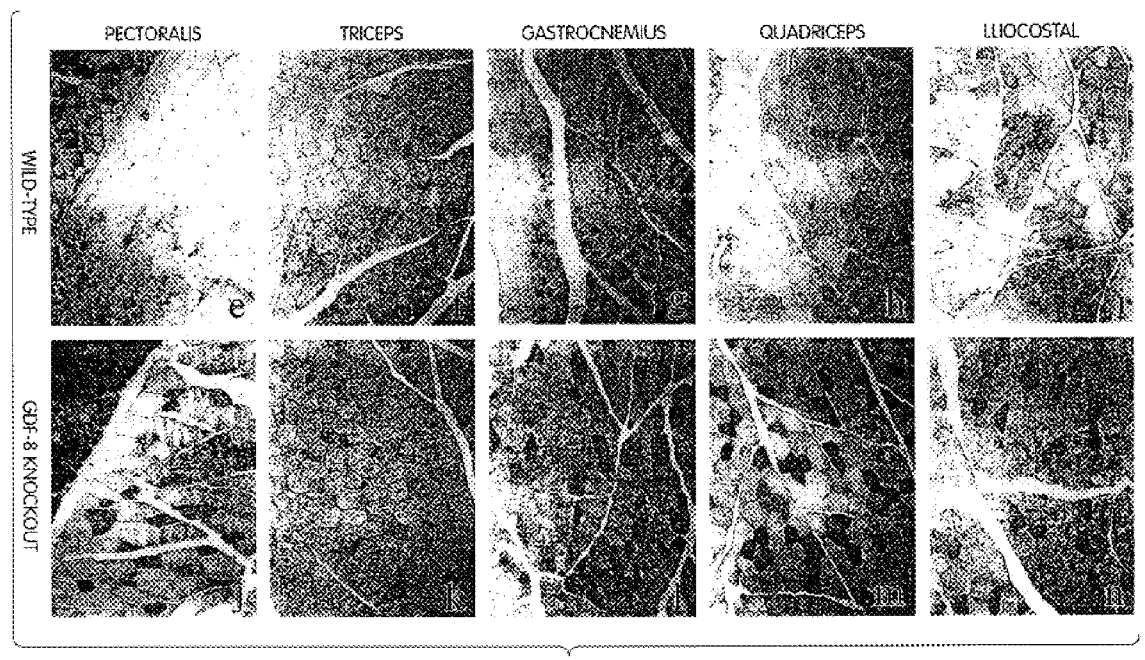
FIG. 1B shows GLUT4 levels, by immunostaining, with an anti-GLUT4 antibody, in five different muscle samples, pectoralis, triceps, gastrocnemius, quadriceps, and iliocostal, in both a wild-type mouse and a GDF-8 knockout mouse.

As shown in FIGS. 1A and 1B, GDF-8 knockout mouse samples display significantly increased GLUT4 expression (as indicated by significantly increased staining with anti-GLUT4 antibody) compared to wild-type samples, regardless of the type of muscle examined. This indicates that GDF-8 causes a decrease in the expression of GLUT4 in these mice.

EXAMPLE 2

Effect of GDF-8 Administration on GLUT4 Protein Expression in Muscle Cells

The following study was performed to assess the converse of what was found in Example 1, i.e., whether exogenous GDF-8 represses the expression of GLUT4 in muscle cells (as predicted from Example 1), and also whether administration of GDF-8 can counteract the effects of the GLUT4 stimulator, insulin.

Mice were randomized to receive either an intramuscular (gastrcenemius muscle) injection of fifty microliters, containing 5 micrograms of recombinant human GDF-8 (in buffer containing 20 mM $NaPO_4$, 150 mM NaCl, 0.1 mg/ml BSA, pH 6.5), or buffer alone. Twenty minutes later mice received an intraperitoneal injection of either porcine insulin purchased from Sigma Chemicals, St. Louis, Mo. (13 Units/ kg in 0.1 ml of the same buffer used above but at pH 7.0), or buffer alone. One hour after insulin administration the animals were sacrificed and samples of the injected muscle were removed.

Figure 2:
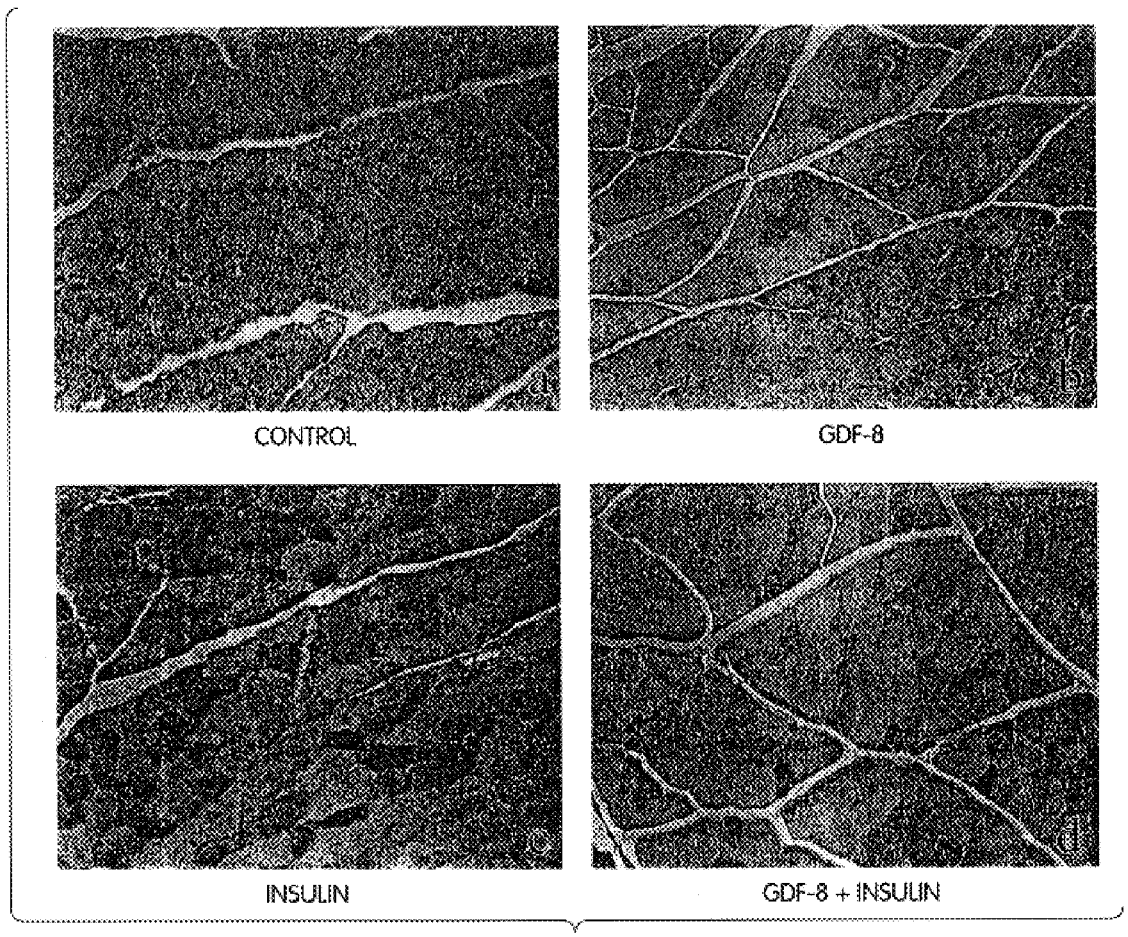
FIG. 2 shows GLUT4 levels by immunostaining with an anti-GLUT4 antibody in muscle from a control mouse, a GDF-8-dosed mouse, an insulin-dosed mouse, and a GDF-8 plus insulin-dosed mouse.

As shown in FIG. 2, the administration of exogenous GDF-8 alone results in a significant decrease in GLUT4 expression in mouse gastrocnemius cells. In contrast, the administration of insulin alone results in the opposite effect—a significant increase in GLUT4 expression (i.e., staining) is observed in these cells. When GDF-8 and insulin are simultaneously administered, the GLUT4 staining pattern appears close to that of untreated control cells, suggesting that these two molecules have opposite regulatory effects on GLUT4.

EXAMPLE 3
Effect of GDF-8-Expressing CHO Cell Tumors in Nude Mice

The results from the preceding Examples indicate that GDF-8 plays an important role in the regulation of GLUT4 protein expression in muscle cells. To further examine the role of GDF-8 in the regulation of overall glucose metabolism in vivo, a Chinese Hamster Ovarian (CHO) tumor cell line producing human GDF-8 (hGDF-8) was injected into nude mice to form a tumor expressing GDF-8. This CHO tumor cell injection approach has been used as a model for determining the effects of various gene products in vivo (Black et al., Endocrinology 123:2657–2659 (1991)).

CHO cells expressing hGDF-8 were cultured in alpha medium with 0.1 micromolar methotrexate and 1 mg/ml G418, while the control CHO cells (containing an empty expression vector) were cultured in alpha medium with 0.1 micromolar methotrexate. The cells were harvested by trypsinization and resuspended in PBS at a concentration of $2 \times 10^7$ cells/ml. A subcutaneous injection of $1 \times 10^7$ cells in 0.5 ml was made into the right thigh of male nu/nu NCR mice. Body weight and tumor sizes were measured twice a week for the duration of the experiment. Northern blot analysis of mRNA isolated from the CHO GDF-8 tumors confirmed that GDF-8 was expressed.

Figure 3:
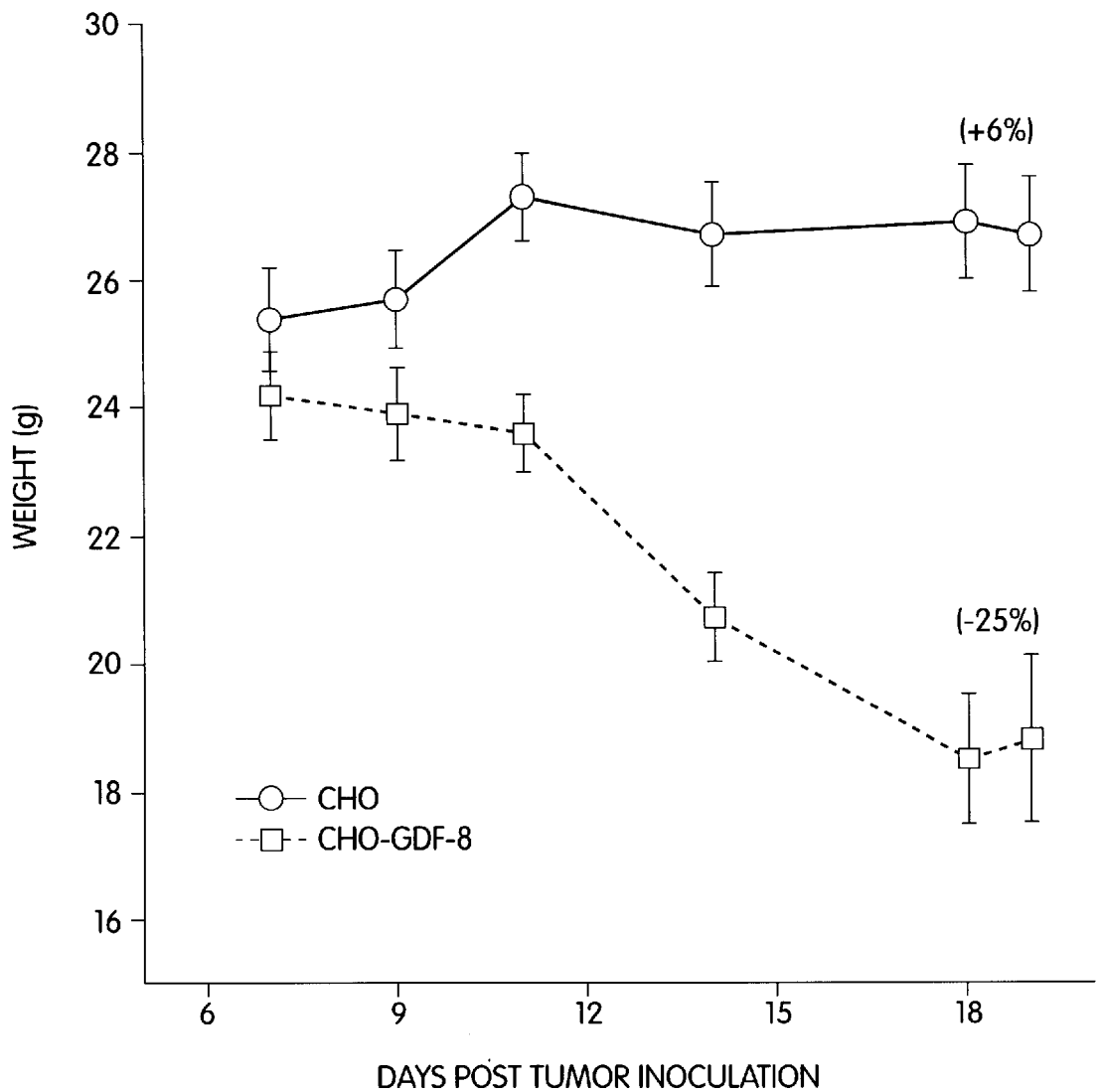
FIG. 3 is a graph showing the correlation between increased systemic levels of GDF-8 in nude mice (as secreted from a GDF-8-expressing CHO cell tumor) and severe weight loss as compared to control mice.
Figure 4A:
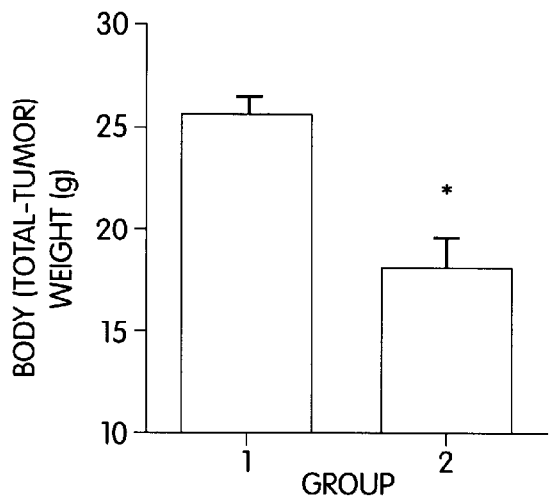
FIG. 4 is a graph showing the correlation between increased systemic levels of GDF-8 in nude mice (as secreted from a GDF-8-expressing CHO cell tumor) and overall body weight (Panel A), tumor weight (Panel B), pectoralis weight (Panel C), epididymal fat weight (Panel D) and gastrocnemius weight (Panel E) as compared to these tissues from control mice containing CHO cell tumors not expressing GDF-8.
Figure 4B:
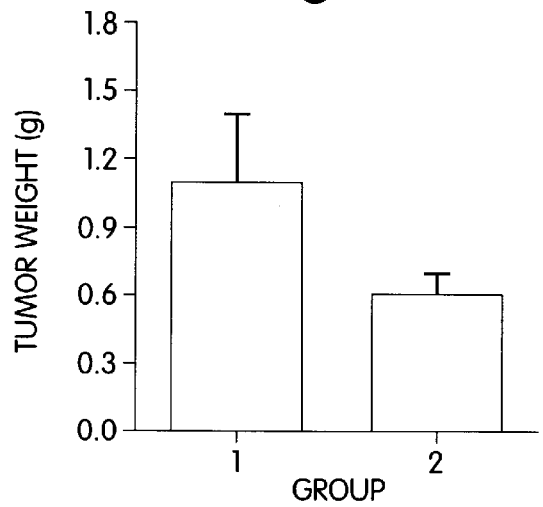
Figure 4C:
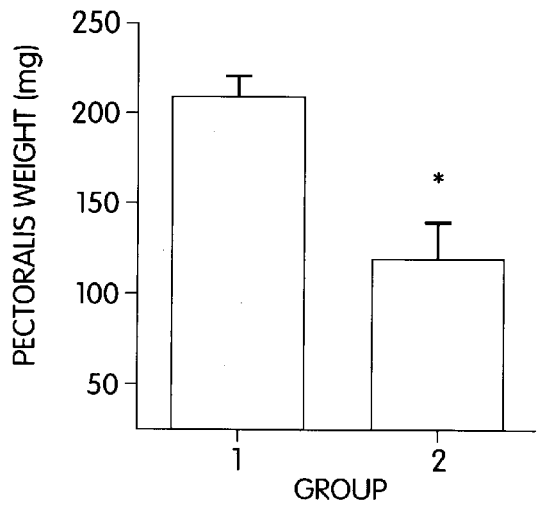
Figure 4D:
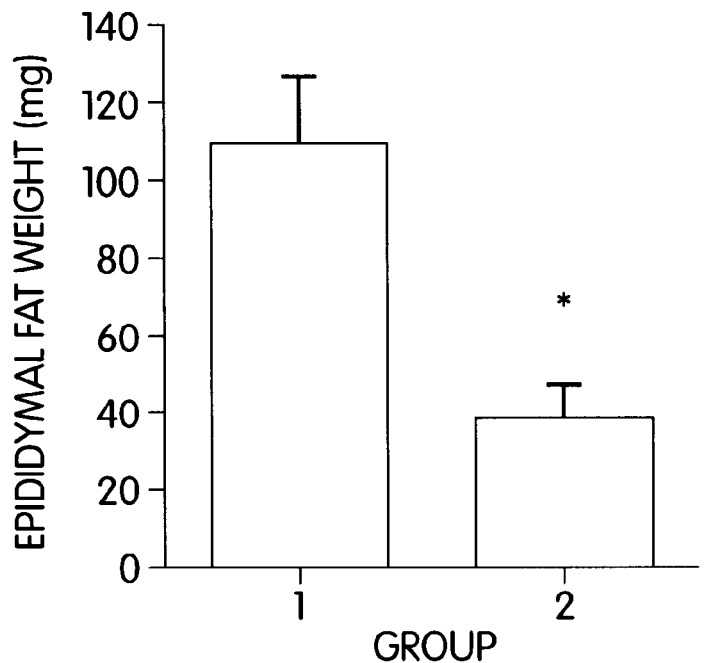
Figure 4E:
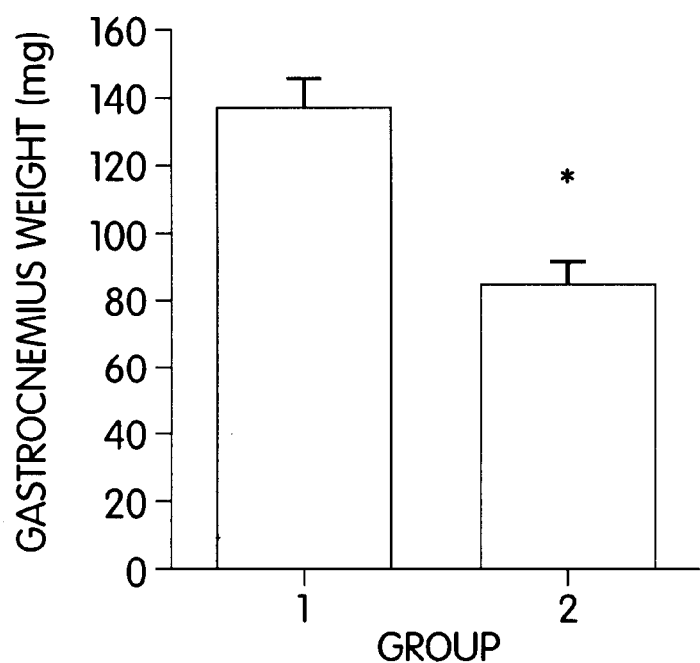

The systemic effects of the GDF-8 produced by the developing CHO GDF-8 tumor were assessed. As shown in FIG. 3, the CHO tumors overexpressing GDF-8 caused dramatic total body weight loss (a decrease of 25%) within 20 days in the nude mice, compared to their weight at the onset of the experiment. In contrast, the mice harboring control CHO tumors not expressing GDF-8 had a slight weight gain (FIG. 3).

Figure 5:
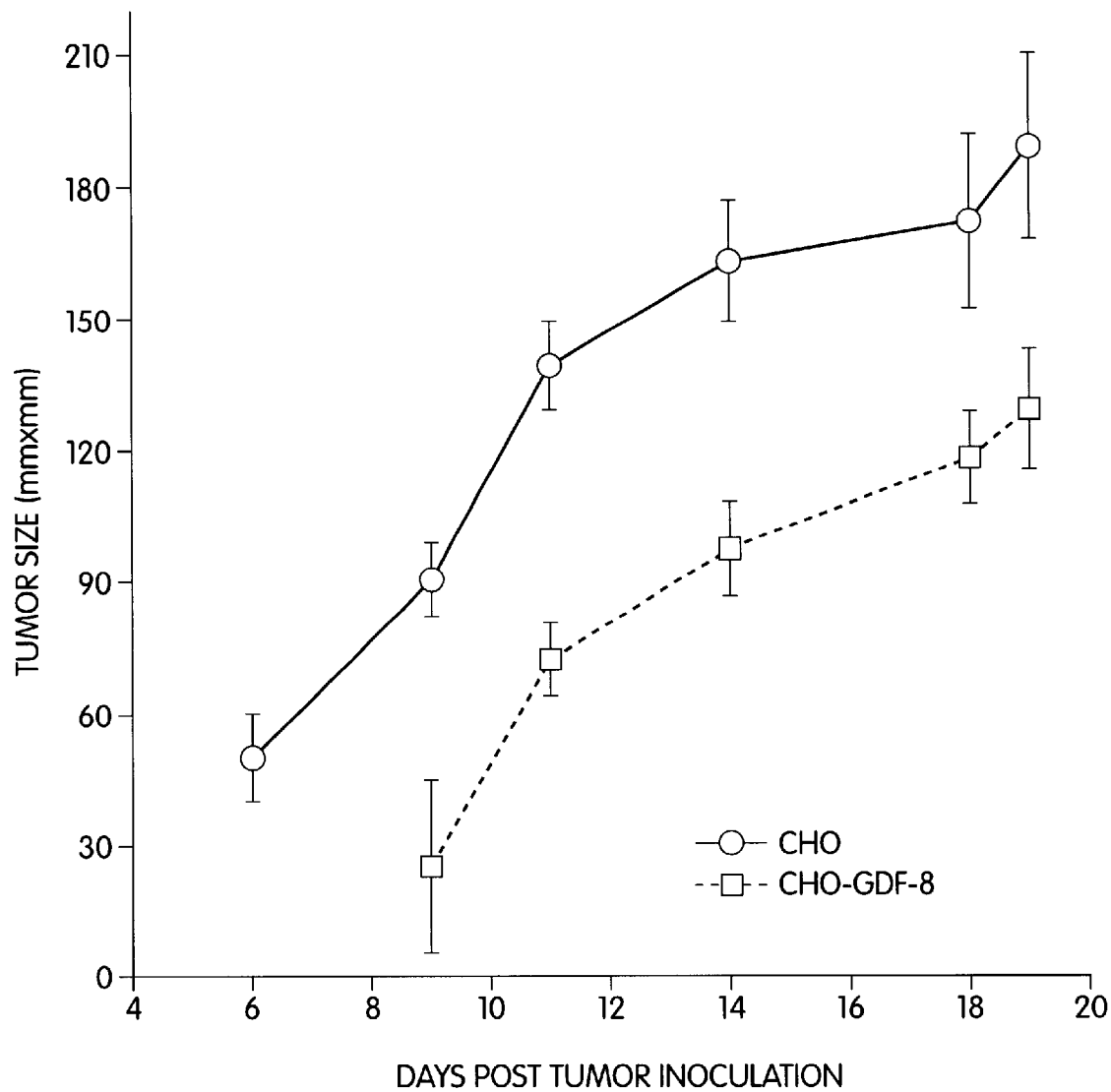
FIG. 5 is a graph comparing the size of GDF-8-secreting CHO cell tumors in nude mice relative to control CHO cell tumors not expressing GDF-8. Tumor size was measured as cross sectional area.

As shown in FIG. 4, the CHO GDF-8 tumor-bearing mice showed an even more dramatic weight loss (35%) when the net body weights (total-tumor) were compared with that of control tumor-bearing mice (FIG. 4, Panel A). The weight loss was not due to the size of the CHO GDF-8 tumor, since control tumor weight was actually heavier than CHO GDF-8 tumor (FIG. 4, Panel B, and FIG. 5).

Individual tissues from CHO and CHO GDF-8-expressing tumor-bearing animals were also isolated and weighed. Muscles and fat pads from CHO GDF-8 tumor-bearing animals showed a significant decrease in weight compared to CHO tumor-bearing animals (FIG. 4, Panels C,D, and E). This general wasting and reduction in skeletal muscle mass demonstrates that the GDF-8 protein produced from implanted CHO cells acts in a manner strictly compatible with, and as expected from, the results of the GDF-8 knock-out approach.

Figure 6A:
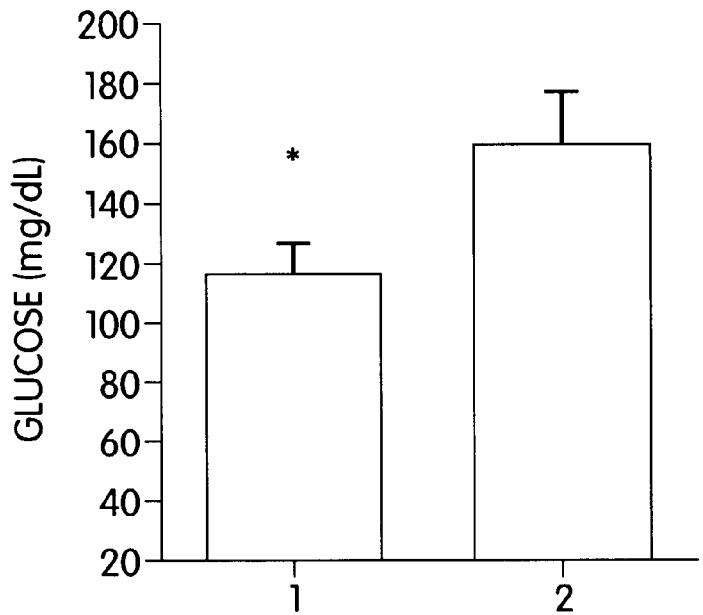
FIG. 6 is a graph showing the correlation between increased GDF-8 levels (from GDF-8 expressing CHO cell tumors) in nude mice and serum glucose levels (Panel A) and GLUT4 expression levels (Panel B) in muscle, as compared to control mice containing CHO cell tumors not expressing GDF-8.
Figure 6B:
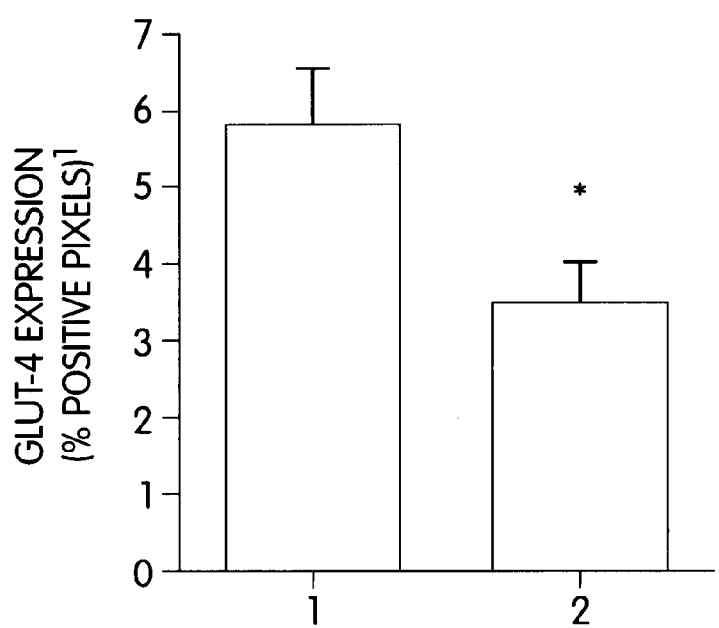

To assess whether GDF-8 is involved in systemic glucose handling, wild-type nude mice carrying CHO-GDF-8 tumors were tested for elevated glucose. As shown in FIG. 6, when compared to control CHO tumor-bearing mice, CHO GDF-8 tumor-bearing animals exhibited hyperglycemia and a significant decrease in GLUT4 levels in muscle tissues. Taken together with the fact that the GDF-8 knock-out mice were hypoglycemic and had increased GLUT4 expression levels in muscle, these results suggested that GDF-8 increases glucose levels in the serum by inhibiting GLUT4 levels in vivo.

EXAMPLE 4
Systemic Effects of GDF-8 Knockout in Mice

Transgenic mice in which the GDF-8 gene is knocked out had characteristic systemic problems, particularly hypoglycemia, significant muscle hypertrophy, and a dramatic decrease in overall body fat. These findings indicate not only that the modulation of GDF-8 may enable the regulation of glucose levels in the serum, thus serving as a treatment for diabetes, but also that GDF-8 may be useful in treating obesity and other disorders related thereto.

While GDF-8 knock-out mice provide a model for postulating the general role of GDF-8 in regulating muscle and fat growth and metabolic function, it is unclear whether the observed changes are a consequence of embryonic GDF-8 deficiency or the result of post-natal development. Thus, this Example, as well as the immediately preceding Example (i.e., Example 3) demonstrate for the first time that GDF-8 has an important physiological role in the adult animal. These two examples provide unambiguous support to the concept that modulating GDF-8 expression and activity post-natally is a means of regulating muscle and fat growth and metabolic function including, but not limited to, muscle growth, glucose homeostasis and diabetes susceptibility.

EXAMPLE 5
Effect of GDF-8 on the Differentiation of 3T3-L1 Pre-Adipocytes

To better characterize the effects of GDF-8 on glucose homeostasis, 3T3-L1 cells were utilized as a model for adipocytes, a cell type acutely responsive to insulin through its ability to increase hexose transport through GLUT4. These cells have been well characterized as an excellent model for adipogenesis (Hwang et al., Annu. Rev. Cell Dev. Biol. 13, 231–259 (1997), and MacDougald and Lane, Annu. Rev. Biochem. 64, 345–373 (1995)). When these cells are stimulated with insulin, dexamethasone and isobutylmethylxanthine (IBMX), they are induced to undergo both morphological and biochemical changes resulting in their differentiation into adipocytes.

When undifferentiated pre-adipocytes reached confluence, differentiation was predictably achieved (Spiegelman et al., J. Biol. Chem. 268: 6823–6826 (1993)) by successive replacements of their serum-containing DMEM media as follows: DMEM+serum+IBMX+ dexamethasone+insulin for 2 days, DMEM+serum+insulin for 2 additional days. After this, the media was again replaced with DMEM+/−serum. GDF-8 and other growth factors were added at the onset of differentiation and were resupplied at each additional medium change. Adipocytes were maintained for an additional 3 to 5 days in this media for full differentiation to take place.

Figure 7:
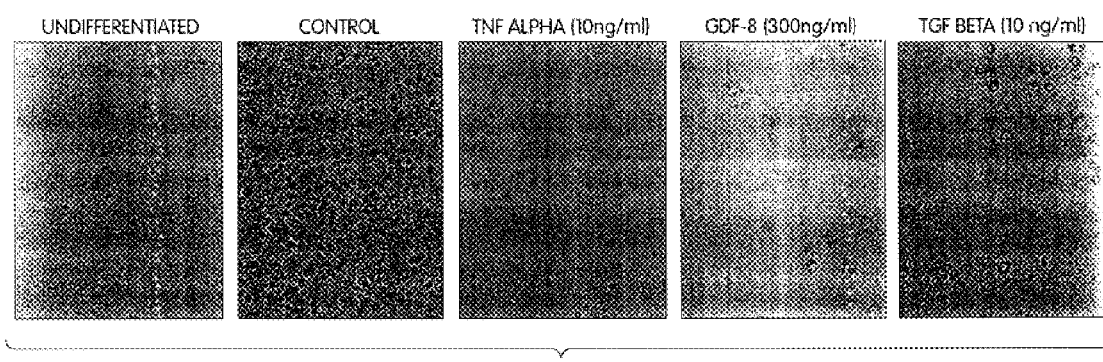
FIG. 7 shows the effect of exogenously added GDF-8 on 3T3-L1 adipocyte differentiation, as compared to no treatment, TNF-α treatment, and TGF-β1 treatment.
Figure 8:
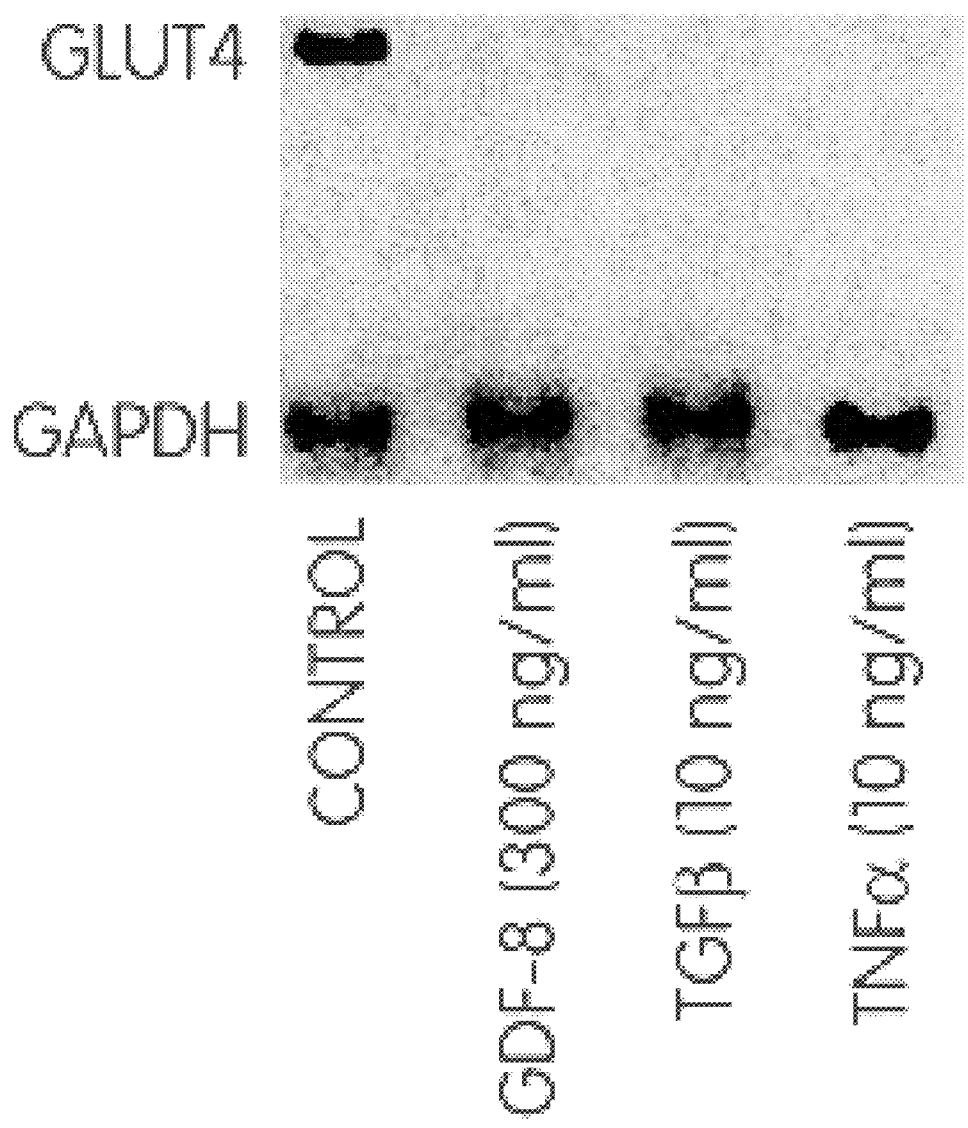
FIG. 8 is a Northern blot analysis showing reduced expression of GLUT4 in 3T3-L1 cells treated with GDF-8, TGFβ and TNFα. Total cellular RNA for each sample was fractionated, immobilized to a membrane and hybridized with $^{32}P$ probes for GLUT4 mRNA.

As shown in FIG. 7, GDF-8 inhibited differentiation of these 3T3-L1 pre-adipocytes to adipocyte cells. The addition of GDF-8 to 3T3-L1 cells at the onset of induction to differentiate into adipocytes prevented the conversion of pre-adipocytes to adipocytes, as seen by the maintenance of pre-adipocyte morphology and the near-absence of refractile cells that contain lipid droplets (FIG. 7). In addition, as shown in FIG. 8, at the RNA level, GDF-8 inhibited the expression of GLUT4 mRNA, a known adipocyte marker.

FIG. 7 also shows that GDF-8 is able to mimic the effects of both TNF-α and TGF-$β_1$ on GLUT4 mRNA levels. Importantly, GLUT4 is known to be the key molecule responsible for insulin-sensitive glucose transport not only in muscle tissue, but also in fat cells. Thus GDF-8 plays a role in mediating insulin resistance associated with Type II diabetes. GDF-8, which is specifically expressed in the muscle and in fat, can fully mimic the previously established effects of two broadly-expressed cytokines, namely TNF-α and TGF-β, on adipocyte differentiation and metabolism (Szalkowski et al., *Endocrinology* 136: 1474–1481 (1995)). Due to its specific expression, GDF-8 may be, among the three, the physiologically most relevant polypeptide that regulates such processes in vivo.

EXAMPLE 6
Effect of GDF-8 on Glucose Uptake in 3T3-L1 Adipocytes

In differentiated adipocytes, insulin stimulates glucose transport through the GLUT4 transporter in a dose-dependent fashion. Thus, the ability of GDF-8 to interfere with this insulin-dependent glucose uptake mechanism was examined as follows.

Upon completion of differentiation, a glucose transport assay was performed on 3T3-L1 cells. GDF-8 was added in the final 72 hours of differentiation. Insulin was added in Krebs-Ringer solution for 20 min., followed by addition of [$^3$H]-deoxyglucose (1 mCi/ml) for 10 min. After extensive washing, cells were lysed with Triton X-100 and the cell-associated radioactive glucose (due to GLUT4 -mediated uptake) was determined by scintillation counting.

Figure 9:
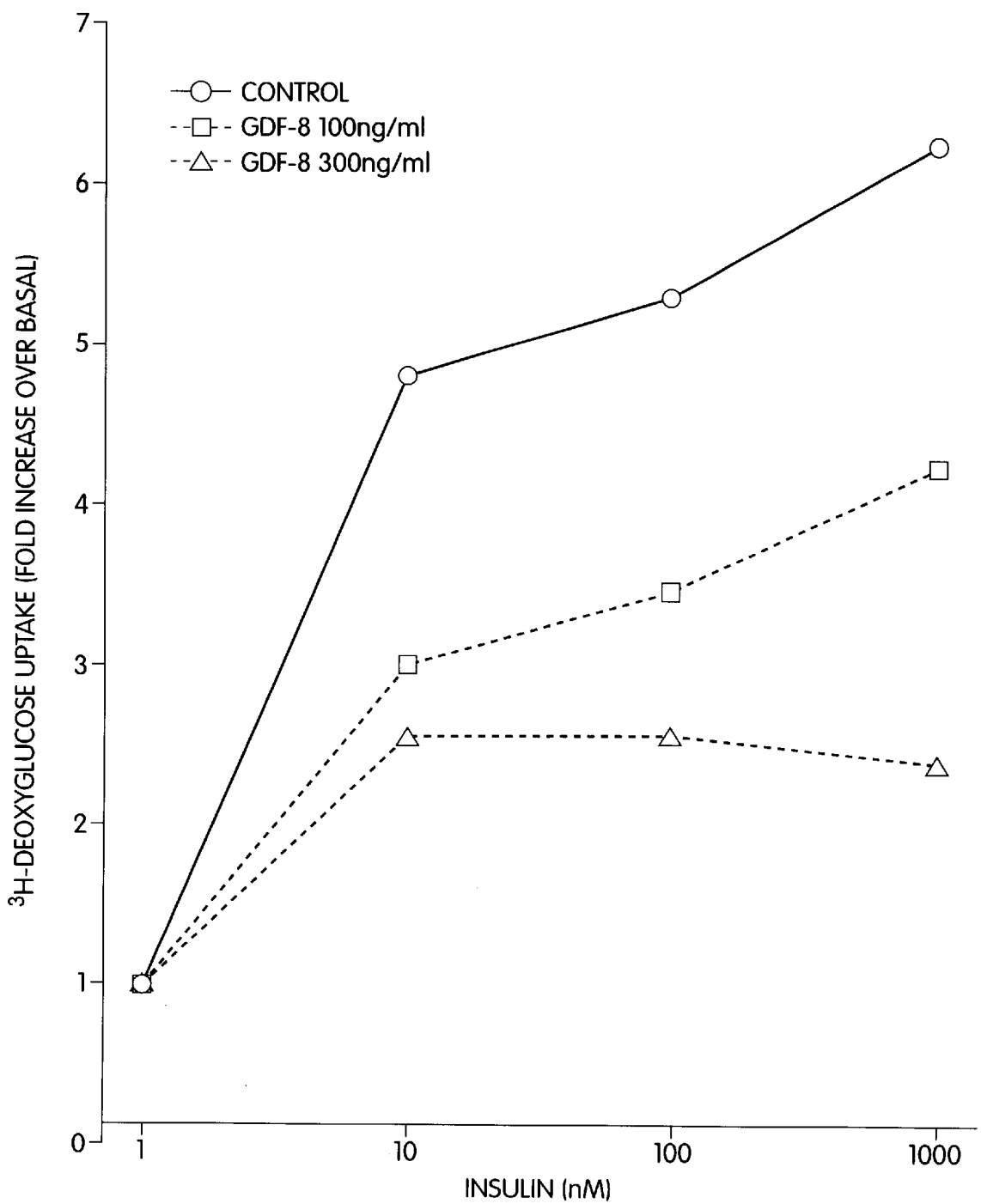
FIG. 9 is a graph showing that treatment of differentiated 3T3-L1 adipocytes with different doses of GDF-8 impairs the ability of these cells to increase glucose uptake in response to insulin, thus leading to desensitization.

As shown in FIG. 9, GDF-8 reduced the insulin-sensitivity of these cells, as measured by fold-induction of glucose uptake, in a dose-dependent manner. This reduced insulin-sensitivity of glucose transport correlated with the decrease of GLUT4 mRNA levels in these cells after GDF-8 treatment (FIG. 8). Thus, this assay offers an in vitro correlate of GDF-8 activity that may be relevant to its in vivo effects on body fat and muscle metabolic functions.

Besides a decrease in the GLUT4 mRNA levels (seen in FIG. 8), an additional important observation was made that in the 3T3-L1 cells, GDF-8 actually increased basal glucose transport by about 50%. This increase in baseline should also contribute to the reduced fold-increases in glucose uptake in response to insulin. Since this basal transport is mainly effected by the ubiquitous GLUT1 transporter (another hexose transporter), it indicates that the insulin insensitivity observed after GDF-8 treatment in adipocytes can stem from a combination of an increase in basal transport (through GLUT1 and other glucose transporters) and a concomitant decrease in insulin-stimulated transport (through GLUT4). However, the increase in basal level of glucose is not limited to the effect of GLUT1. Additional glucose transporters can also increase the basal level of glucose in the 3T3-L1 cells.

EXAMPLE 7
Effect of GDF-8 in Diabetes Disease Models

The foregoing Examples demonstrate that GDF-8 inhibition can increase GLUT4 transcription and expression, and thereby restore insulin sensitivity and reduce systemic glucose levels in a subject. The foregoing Examples further demonstrate that GDF-8 inhibition upregulates differentiation of adipocytes, and thereby increases insulin-sensitive glucose uptake.

Together, this data suggests that interfering with GDF-8 function could have important applications for the treatment of Type II diabetes, obesity and disorders related to obesity. To pursue these potential applications, the following approaches can be taken.

A. Analysis of the Effect of the GDF-8 Mutation in Mouse Models of Obesity/Diabetes GDF-8 knockout mice can be crossed with various mouse strains exhibiting obesity, particularly ob/ob, db/db, and mice carrying the lethal yellow mutation. Serum levels of known molecular markers of obesity, such as glucose, insulin, lipids, and creatine kinase are monitored and compared to control animals lacking the GDF-8 knockout, as an indication of the presence of this condition in the test animals. Functional assays for diabetes/obesity including, but not limited to, an insulin sensitivity assay, a glucose tolerance assay and an ex-vivo glucose uptake by isolated muscle assay also can be performed to monitor the effect of GDF-8 knockout on progeny mice.

In progeny mice carrying both the GDF-8 knockout and the recessive obesity genotype, the lack of GDF-8 should suppress the obesity phenotype as compared to that of corresponding control mice, as measured by serum levels of known molecular markers of obesity, such as glucose, insulin, lipids and creatine kinase. Additionally, the development of diabetes in these animals should be delayed or prevented by the absence of GDF-8.

B. Analysis of GDF-8 Knockout Mice in Various Models of Diabetes

GDF-8 knockout mice can be subjected to agents capable of inducing experimental diabetes, such as streptozotocin. An analysis of serum levels of molecular diabetes markers, such as glucose, insulin, lipids, and creatine kinase is performed in these animals, and compared to, e.g., streptozotocin-treated wild-type control animals. Functional assays for diabetes/obesity including, but limited to, an insulin sensitivity assay, a glucose tolerance assay and an ex-vivo glucose uptake by isolated muscle assay can be performed to monitor the effect of streptozotocin on the treated and non-treated animals. The GDF-8 knockout mice should be relatively resistant to such treatments, and the onset of experimental diabetes should be altogether prevented, delayed, or be less severe.

C. Demonstration of the Efficacy of GDF-8 Inhibitors in Mouse Models of Obesity/Diabetes Mice serving as models for obesity or diabetes can be treated with GDF-8 inhibitors to determine whether inhibition of GDF-8 and the corresponding impact on GLUT4 ameliorates the symptoms of either obesity or diabetes in these animals.

Mice with either obesity or diabetes are treated with one or more GDF-8 inhibitors in a therapeutically effective dose. GDF-8 levels in treated and control mice can be assessed by Western blot analysis using antibodies specific for GDF-8. Levels of molecules characteristic for obesity and diabetes, such as glucose, insulin, lipids, and creatine kinase can be assessed in serum samples taken from treated and control animals. Functional assays for diabetes/obesity including, but not limited to, an insulin sensitivity assay, a glucose tolerance assay and an ex-vivo glucose uptake by isolated muscle cell assay can be performed to monitor the effect of the inhibitor on treated and non-treated animals. Similarly, muscle and fat cell differentiation can be observed in these animals. Analysis of such studies should enable a determination of the overall effect of the inhibition of GDF-8 on the progression of diabetes or obesity in animal models for these diseases.

All patents, published patent applications and other published references disclosed herein are hereby expressly incorporated herein in their entireties by reference.

Equivalents

Those skilled in the art will recognize, or will be able to ascertain using no more than routine experimentation, many equivalents to the specific embodiments of the invention described herein. Such equivalents are intended to be encompassed by the following claims.

We claim:

1. A method of increasing expression of GLUT4 in a subject comprising administering to the subject a GDF-8 antibody or fragment thereof.

2. A method of increasing insulin sensitivity and glucose uptake by cells in a subject comprising administering to the subject a GDF-8 antibody or fragment thereof.

3. A method of treating diabetes in a subject comprising administering to the subject a GDF-8 antibody or fragment thereof.

4. The method of claim 2, wherein said insulin sensitivity and glucose uptake is increased by modulating the expression of a hexose transporter selected from the group consisting of GLUT4 and GLUT1.

5. The method of claim 3, wherein the subject is suffering from type II diabetes.

6. A method of increasing insulin sensitivity and glucose uptake by a muscle cell or a precursor thereof, in a subject comprising administering to the subject a GDF-8 inhibitor.

7. A method of increasing insulin sensitivity and glucose uptake by an adipocyte or a precursor thereof, in a subject comprising administering to the subject a GDF-8 inhibitor.

* * * * *

UNITED STATES PATENT AND TRADEMARK OFFICE
CERTIFICATE OF CORRECTION

PATENT NO.    : 6,368,597 B1
DATED         : April 9, 2002
INVENTOR(S)   : Gideon Strassmann et al.

It is certified that error appears in the above-identified patent and that said Letters Patent is hereby corrected as shown below:

<u>Title page,</u>
Item [73], please delete "Matamorphix, Inc." and insert -- Metamorphix, Inc --.

Signed and Sealed this

Eleventh Day of June, 2002

Attest:

JAMES E. ROGAN
*Attesting Officer*    *Director of the United States Patent and Trademark Office*